US012673181B2

(12) United States Patent
Pytel et al.

(10) Patent No.: US 12,673,181 B2
(45) Date of Patent: Jul. 7, 2026

(54) INTERMITTENT CATHETERS

(71) Applicant: ConvaTec Limited, Deeside (GB)

(72) Inventors: Rachel Zimet Pytel, Newton, MA (US); Neal Robert Carty, Las Vegas, NV (US); Lukas Kandrac, Michalovce (SK)

(73) Assignee: CONVATEC LIMITED, Flintshire (GB)

( * ) Notice: Subject to any disclaimer, the term of this patent is extended or adjusted under 35 U.S.C. 154(b) by 631 days.

(21) Appl. No.: 17/871,440

(22) Filed: Jul. 22, 2022

(65) Prior Publication Data

US 2023/0033481 A1    Feb. 2, 2023

Related U.S. Application Data

(63) Continuation of application No. PCT/GB2022/051922, filed on Jul. 22, 2022.

(60) Provisional application No. 63/203,590, filed on Jul. 27, 2021.

(51) Int. Cl.
*A61M 25/00*    (2006.01)

(52) U.S. Cl.
CPC .... *A61M 25/0017* (2013.01); *A61M 25/0043* (2013.01); *A61M 25/002* (2013.01)

(58) Field of Classification Search
CPC .......... A61M 25/0017; A61M 25/0009; A61M 2025/0062; A61M 2205/0216; A61M 2205/0222; A61M 2205/025; A61M 2207/10; A61L 29/085; A61L 29/14; A61L 29/041
See application file for complete search history.

(56) References Cited

U.S. PATENT DOCUMENTS

| | | | | |
|---|---|---|---|---|
| 7,708,774 | B1 * | 5/2010 | Tan | A61L 27/26 |
| | | | | 428/447 |
| 11,904,111 | B2 | 2/2024 | Donnelly et al. | |
| 11,957,614 | B2 | 4/2024 | Kendrick et al. | |
| 11,980,721 | B2 | 5/2024 | Hilton et al. | |
| 2005/0100580 | A1 * | 5/2005 | Osborne | A61L 31/16 |
| | | | | 623/1.42 |
| 2005/0271700 | A1 * | 12/2005 | DesNoyer | A61L 31/10 |
| | | | | 427/2.24 |
| 2006/0240060 | A1 * | 10/2006 | Bavaro | A61L 29/085 |
| | | | | 424/422 |
| 2007/0016169 | A1 * | 1/2007 | Utas | A61L 29/14 |
| | | | | 427/2.1 |
| 2009/0155575 | A1 * | 6/2009 | Dias | C08J 7/056 |
| | | | | 428/419 |
| 2010/0146715 | A1 * | 6/2010 | Ellis | A61K 8/8111 |
| | | | | 8/160 |
| 2012/0109036 | A1 * | 5/2012 | Sambasivam | C09J 183/00 |
| | | | | 526/279 |
| 2012/0219742 | A1 * | 8/2012 | Gravesen | A61L 31/041 |
| | | | | 525/88 |
| 2013/0158517 | A1 * | 6/2013 | Bouchard | A61L 29/085 |
| | | | | 604/533 |
| 2013/0261566 | A1 * | 10/2013 | Lockwood | A61L 29/14 |
| | | | | 523/105 |
| 2013/0289531 | A1 * | 10/2013 | Pagan | A61L 29/126 |
| | | | | 525/190 |
| 2014/0141048 | A1 * | 5/2014 | Rolf | A61L 29/16 |
| | | | | 514/56 |
| 2015/0297862 | A1 * | 10/2015 | Sadik | A61M 25/0009 |
| | | | | 604/544 |
| 2015/0335856 | A1 * | 11/2015 | Utas | B65B 3/04 |
| | | | | 53/436 |
| 2015/0359947 | A1 * | 12/2015 | Hossainy | A61L 31/06 |
| | | | | 264/328.14 |
| 2016/0022877 | A1 | 1/2016 | Gravesen et al. | |
| 2016/0250388 | A1 * | 9/2016 | Wang | A61L 31/16 |
| | | | | 604/103.02 |
| 2018/0043066 | A1 * | 2/2018 | Grinstaff | A61L 31/10 |
| 2019/0224384 | A1 * | 7/2019 | Lundahl | A61L 29/14 |
| 2021/0069090 | A1 * | 3/2021 | Cass | A61K 8/31 |
| 2022/0041886 | A1 * | 2/2022 | Jiang | C09D 133/26 |
| 2022/0119724 | A1 * | 4/2022 | Ge | C10M 125/22 |
| 2022/0218879 | A1 * | 7/2022 | Lewitus | A61L 29/085 |
| 2024/0075243 | A1 | 3/2024 | Lovmar | |
| 2024/0218176 | A1 * | 7/2024 | Jonsman | A61L 31/06 |

FOREIGN PATENT DOCUMENTS

| | | | | |
|---|---|---|---|---|
| CN | 102639160 A | 8/2012 | | |
| CN | 111569159 A | * 8/2020 | .......... | A61L 29/106 |
| EP | 4062952 B1 | 1/2024 | | |

OTHER PUBLICATIONS

Ge, S., Chen, J., Werner, S., Pham, H., & Savargaonkar, N. (2010). Migration of Additives in Polyolefin Films Characterized by AFM. Microscopy and Microanalysis, 16(S2), 478-479.*

Llop et al., "Control of the Migration Behavior of Slip Agents in Polyolefin-Based Films", Polymer Engineering & Science, vol. 51, No. 9, pp. 1763-1769, Mar. 23, 2011, DOI: 10.1002/pen.21963.

Chinese Office Action; Chinese Patent Office; CN Patent Application No. 202280049263.4; Apr. 28, 2026; 19 pages.

* cited by examiner

*Primary Examiner* — Adam Marcetich

(74) *Attorney, Agent, or Firm* — TAFT STETTINIUS HOLLISTER LLP; Ryan O. White; Derek B. Lavender

(57) ABSTRACT

The invention provides an intermittent catheter comprising a hollow polymeric tubular body comprising a base polymer and a lubricious additive, wherein the lubricious additive comprises an amphiphilic molecule having a hydrophilic-lipophilic balance below 8.

17 Claims, No Drawings

INTERMITTENT CATHETERS

CROSS REFERENCE TO RELATED DISCLOSURES

The present disclosure is a continuation of International Application No. PCT/GB2022/051922 filed on Jul. 22, 2022 and claims the benefit of U.S. Provisional Application No. 63/203,590 filed on Jul. 27, 2021, the contents of which are incorporated herein by reference.

TECHNICAL FIELD OF THE INVENTION

The present invention relates to intermittent catheters comprising a base polymer and an amphiphilic lubricious additive.

BACKGROUND TO THE INVENTION

Intermittent urinary catheterisation is a process involving insertion of a urinary catheter through an individual's urethra and into their bladder, where it is retained to empty the bladder of urine for only the time period that is required for emptying, after which the catheter is removed. The process differs from long-term catheterisation, which makes use of an indwelling or Foley catheter that is inserted into the bladder for long periods of time (several days to months) to discharge the residual urine of the bladder continuously throughout the day.

Intermittent catheterisation is often used by patients suffering from abnormalities of the urinary system, resulting in urinary incontinence and/or a lack of control in permitting voluntary urination. Such individuals would typically make use of intermittent catheters several times a day.

Intermittent catheters are useful devices, providing users with independence and freedom to self-catheterise as and when required, without having to rely on trained personnel to be present. This, however, increases the need for intermittent catheters to be user friendly: in particular, both easy to insert and remove with minimum discomfort caused, and safe to use with features for minimising risk of infection. Users often report experiencing pain and discomfort upon insertion and/or removal of intermittent catheters. Users have, for instance, reported experiencing bladder spasms, burning sensations, and bleeding. Urinary tract infections (UTI) are also common in individuals who practice intermittent catheterisation.

Surface coatings and additives for intermittent catheters have been used to help in alleviating these issues. However, intermittent catheter surface coatings and additives have the tendency to migrate out of the catheter with time and use, which causes the surface of the catheter to become less lubricious. Often coatings and additives may migrate out of a catheter even when the catheter is not in use, including when is packaged wet in a storage or transportation medium. This has made it challenging for intermittent catheters to be packaged in direct contact with a wetting agent. Often a wetting agent must be packaged in a separate container or sachet, which requires the use of increased amounts of packaging (thus generating more waste) and necessitates an added inconvenient step for the user to apply the wetting agent to the intermittent catheter.

In use, scraping of the catheter surface may occur, further accelerating the removal of any surface coatings or additives.

Furthermore, when a person uses an intermittent catheter, some of the coating may be left inside the user's body, which can be harmful and thus unacceptable.

To address some of the above problems, U.S. Pat. Nos. 10,058,638 B2 and 9,186,438 B2 describe the use of a catheter containing a polymer mixture of a thermoplastic or thermo-curing polymer base material and an amphiphilic block copolymer lubricious additive. The amphiphilic block copolymer contains both a hydrophobic and hydrophilic portion. The hydrophilic portion diffuses to the surface of the catheter due to incompatibility with the hydrophobic base material and provides for a lubricious surface coating. Interactions between the hydrophobic portion of the amphiphilic molecule and the base material assist in reducing migration of the amphiphilic molecule from the catheter. However, strong hydrophilic-hydrophilic interactions between the hydrophilic portion of the lubricious additive and a hydrophilic external environment can at times overcome the hydrophobic-hydrophobic interactions between the hydrophobic portion of the additive and the hydrophobic base material, causing the additive to migrate out of the catheter.

There exists a need for catheters with further safeguards to reduce migration of surface coatings and additives from the catheter. There is a particular need for intermittent catheters that can be packaged in a storage or transportation medium with reduced migration of surface coatings and additives from the catheters.

It is an aim of embodiments of the present invention to address one or more of the above problems by providing an intermittent catheter, suitable for self-catheterisation use, which provides one or more of the following advantages:

A lubricous, non-stick surface making the intermittent catheter easier to insert and remove.

Retention of a lubricious, non-stick surface even when the surface is scraped.

Reduced migration of coatings and additives in the intermittent catheter.

Reduced migration of coatings and additives out of the intermittent catheter when the catheter is not in use, such as when it is packaged wet in a storage or transportation medium.

It is also an aim of embodiments of the invention to overcome or mitigate at least one problem of the prior art, whether expressly described herein or not.

SUMMARY OF THE INVENTION

According to a first aspect of the invention, there is provided an intermittent catheter comprising a hollow polymeric tubular body comprising a base polymer and a lubricious additive, wherein the lubricious additive comprises an amphiphilic molecule having a hydrophilic-lipophilic balance (HLB) below 8.

The amphiphilic lubricious additive comprises a hydrophobic portion and a hydrophilic portion. A lubricious additive with an HLB of below 8 provides a ratio of the degree to which it is hydrophobic and hydrophilic which allows for hydrophobic-hydrophobic interactions between the hydrophobic portion and the base polymer to overcome the hydrophilic-hydrophilic interactions between the hydrophilic portion and a hydrophilic external environment (often comprising a transportation or wetting agent aqueous solution). This allows for reduced migration of the additive out of the catheter. Such an HLB value nonetheless also allows the hydrophilic portion of the additive to seek towards an outer surface of the intermittent catheter due to its affinity with the hydrophilic external environment and its incompatibility with the hydrophobic base polymer. When the hydrophilic portion of the amphiphilic additive is present at or on the outer surface of the intermittent catheter, it enables wetting of the outer surface simply by applying water or wiping with a wet wipe to create a lubricious coating, which makes the catheter easier and less painful to use, especially for individuals practicing self-catheterisation.

The HLB value of the amphiphilic lubricious additive is calculated using Griffin's method, wherein $HLB=20*M_h/M$ ($M_h$ is the molecular mass of the hydrophilic portion of the amphiphilic molecule, and M is the molecular mass of the whole molecule).

In some embodiments, the amphiphilic molecule has an HLB of no greater than 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6, 5.9, 5.8, 5.7, 5.6, 5.5, 5.4, 5.3, 5.2, 5.1, 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, or of no greater than 2.

In some embodiments, the amphiphilic molecule has an HLB of at least 0.5, 0.6, 0.7, 0.8, 0.9, 1, 1.1, 1.2, 1.3, 1.4, or of at least 1.5.

In some embodiments, the amphiphilic molecule has an HLB of between 0.5-8.

In some embodiments, the amphiphilic molecule has an HLB of between 1-8, 1.5-8, 2-8, 2.5-8, 3-8, 3.5-8, 4-8, 4.5-8, 5-8, 5.5-8, 6-8, 6.5-8, 7-8, or of between 7.5-8.

In some embodiments, the amphiphilic molecule has an HLB of between 0.5-7.5, 0.5-7, 0.5-6.5, 0.5-6, 0.5-5.5, 0.5-5, 0.5-4.5, 0.5-4, 0.5-3.5, 0.5-3, 0.5-2.5, 0.5-2, 0.5-1.5, or of between 0.5-1.

In further embodiments, the amphiphilic molecule has an HLB of between 1-7.5, 1.5-7.5, 2-7.5, 2.5-7.5, 3-7.5, 3.5-7.5, 4-7.5, 4.5-7.5, 5-7.5, 5.5-7.5, 6-7.5, 6.5-7.5, 7-7.5, 1-7, 1.5-7, 2-7, 2.5-7, 3-7, 3.5-7, 4-7, 4.5-7, 5-7, 5.5-7, 6-7, 6.5-7, 1-6.5, 1.5-6.5, 2-6.5, 2.5-6.5, 3-6.5, 3.5-6.5, 4-6.5, 4.5-6.5, 5-6.5, 5.5-6.5, 6-6.5, 1-6, 1.5-6, 2-6, 2.5-6, 3-6, 3.5-6, 4-6, 4.5-6, 5-6, 5.5-6, 1-5.5, 1.5-5.5, 2-5.5, 2.5-5.5, 3-5.5, 3.5-5.5, 4-5.5, 4.5-5.5, 5-5.5, 1-5, 1.5-5, 2-5, 2.5-5, 3-5, 3.5-5, 4-5, 4.5-5, 1-4.5, 1.5-4.5, 2-4.5, 2.5-4.5, 3-4.5, 3.5-4.5, 4-4.5, 1-4, 1.5-4, 2-4, 2.5-4, 3-4, 3.5-4, 1-3.5, 1.5-3.5, 2-3.5, 2.5-3.5, 3-3.5, 1-3, 1.5-3, 2-3, 2.5-3, 1-2.5, 1.5-2.5, 2-2.5, 1-2, 1.5-2, or of between 1-1.5.

The amphiphilic molecule may have an HLB of between 0.5 and 4, between 0.5 and 3 or between 0.5 and 2.

The lubricious additive may comprise an amphiphilic molecule that is polymeric or oligomeric.

In some embodiments, the additive is an A-B block copolymer comprising a hydrophobic hydrocarbon A-block and a hydrophilic B-block. In some embodiments, one or both of the hydrophobic hydrocarbon A-block and the hydrophilic B-block may be branched. The hydrophobic A-block may comprise hydrophobic hydrocarbon chains branching therefrom. The hydrophobic hydrocarbon chains may be of shorter chain lengths than the hydrophobic hydrocarbon A-block. The hydrophilic B-block may comprise further hydrophilic B-blocks branching therefrom.

In some embodiments, the additive is a B-A-B tri-block copolymer comprising a hydrophobic hydrocarbon A-block and hydrophilic B-blocks.

In other embodiments, the additive is graft copolymer. The graft copolymer may preferably comprise a hydrophobic hydrocarbon A-block with hydrophilic B-blocks branching therefrom.

In further embodiments, the additive is a brush copolymer. The additive may comprise a single hydrophilic B-block with more than one hydrophobic hydrocarbon A-block branching from an end thereof. The B-block may comprise 2, 3, 4, 5, 6, 7, 8, 9, 10, or more hydrophobic A-blocks branching from the end thereof.

In all of the above embodiments, the or each hydrophilic B-block may comprise a hydrophilic oligomer, i.e. a homo- or co-oligomer comprising at least one monomer unit. The hydrophilic oligomer may comprise between 2 and 10 monomer units. The at least one monomer unit may be selected from the group comprising: alkylene oxides, alkylene glycols, epihalohydrins, unsaturated carboxylic acids, alkylene imines, lactones, vinyl alcohol, and vinyl alkanoates. The at least one monomer unit may be preferably selected from the group comprising: ethylene oxide, propylene oxide, ethylene glycol, propylene glycol, epichlorohydrin, acrylic acid, methacrylic acid, ethylene imine, caprolactone, vinyl alcohol, and vinyl acetate. In some embodiments, the at least one monomer unit comprises alkylene oxide groups independently selected from ethylene oxide and propylene oxide, and in preferred embodiments, all of the monomer units are ethylene oxide or all of the monomer units are propylene oxide.

In some embodiments, the A-block comprises a hydrocarbon chain block of the formula $CH_3CH_2(CH_2CH_2)_a$ where "a" is at least 26.

In further embodiments, the additive is a star-block or a multi-block copolymer comprising hydrophilic and hydrophobic monomer units.

The amphiphilic lubricious additive preferably comprises an amphiphilic molecule as defined for one or more of the second, third and fourth aspects of the invention below. Statements of invention relating to the intermittent catheter of the second, third and fourth aspects of the invention or to any of its components may also be applied to the first aspect of the invention.

According to a second aspect of the invention, there is provided an intermittent catheter comprising a hollow polymeric tubular body comprising a base polymer and a lubricious additive, wherein the lubricious additive is an amphiphilic molecule comprising hydrophobic and hydrophilic monomer units, and wherein the additive has a hydrophobic to hydrophilic monomer unit ratio of at least 10.

A lubricious additive with such a ratio of hydrophobic to hydrophilic monomer units provides a ratio of the degree to which it is hydrophobic and hydrophilic which allows for hydrophobic-hydrophobic interactions between the hydrophobic portion and the base polymer to overcome the hydrophilic-hydrophilic interactions between the hydrophilic portion and a hydrophilic external environment (often comprising a transportation or wetting agent aqueous solution). This allows for reduced migration of the additive out of the catheter. Such ratios nonetheless also allow the hydrophilic portion of the additive to seek towards an outer surface of the intermittent catheter due to its affinity with the hydrophilic external environment and its incompatibility with the hydrophobic base polymer. When the hydrophilic portion of the amphiphilic additive is present at or on the outer surface of the intermittent catheter, it enables wetting of the outer surface simply by applying water or wiping with a wet wipe to create a lubricious coating, which makes the catheter easier and less painful to use, especially for individuals practicing self-catheterisation.

In some embodiments, the additive has a hydrophobic to hydrophilic monomer unit ratio of at least 10.5, or of at least 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or of at least 25.

In some embodiments, the additive has a hydrophobic to hydrophilic monomer unit ratio of greater than 13.

In some embodiments, the additive has a hydrophobic to hydrophilic monomer unit ratio of no greater than 75, or of no greater than 70, 65, 60, 55, 50, 45, 40, 35, or of no greater than 30.

In some embodiments, the additive has a hydrophobic to hydrophilic monomer unit ratio of between 10-50.

The additive may have a hydrophobic to hydrophilic monomer unit ratio of between 12-50, or of between 14-50, 16-50, 18-50, 20-50, 22-50, 24-50, 26-50, 28-50, 30-50, 32-50, 34-50, 36-50, 38-50, 40-50, 42-50, 44-50, 46-50, or of between 48-50.

The additive may have a hydrophobic to hydrophilic monomer unit ratio of between 10-48, or of between 10-46, 10-44, 10-42, 10-40, 10-38, 10-36, 10-34, 10-32, 10-30, 10-28, 10-26, 10-24, 10-22, 10-20, 10-18, 10-16, 10-14, or of between 10-12.

The additive may have a hydrophobic to hydrophilic monomer unit ratio of between 12-48, or of between 14-48, 16-48, 18-48, 20-48, 22-48, 24-48, 26-48, 28-48, 30-48, 32-48, 34-48, 36-48, 38-48, 40-48, 42-48, 44-48, 46-48, 12-46, 14-46, 16-46, 18-46, 20-46, 22-46, 24-46, 26-46, 28-46, 30-46, 32-46, 34-46, 36-46, 38-46, 40-46, 42-46, 44-46, 12-44, 14-44, 16-44, 18-44, 20-44, 22-44, 24-44, 26-44, 28-44, 30-44, 32-44, 34-44, 36-44, 38-44, 40-44, 42-44, 12-42, 14-42, 16-42, 18-42, 20-42, 22-42, 24-42, 26-42, 28-42, 30-42, 32-42, 34-42, 36-42, 38-42, 40-42, 12-40, 14-40, 16-40, 18-40, 20-40, 22-40, 24-40, 26-40, 28-40, 30-40, 32-40, 34-40, 36-40, 38-40, 12-38, 14-38, 16-38, 18-38, 20-38, 22-38, 24-38, 26-38, 28-38, 30-38, 32-38, 34-38, 36-38, 12-36, 14-36, 16-36, 18-36, 20-36, 22-36, 24-36, 26-36, 28-36, 30-36, 32-36, 34-36, 12-34, 14-34, 16-34, 18-34, 20-34, 22-34, 24-34, 26-34, 28-34, 30-34, 32-34, 12-32, 14-32, 16-32, 18-32, 20-32, 22-32, 24-32, 26-32, 28-32, 30-32, 12-30, 14-30, 16-30, 18-30, 20-30, 22-30, 24-30, 26-30, 28-30, 12-28, 14-28, 16-28, 18-28, 20-28, 22-28, 24-28, 26-28, 12-26, 14-26, 16-26, 18-26, 20-26, 22-26, 24-26, 12-24, 14-24, 16-24, 18-24, 20-24, 22-24, 12-22, 14-22, 16-22, 18-22, 20-22, 12-20, 14-20, 16-20, 18-20, 12-18, 14-18, 16-18, 12-16, 14-16, or of between 12-14.

The lubricious additive may comprise an amphiphilic molecule that is polymeric or oligomeric.

In some embodiments, the additive is an A-B block copolymer comprising a hydrophobic hydrocarbon A-block and a hydrophilic B-block. In some embodiments, one or both of the hydrophobic hydrocarbon A-block and the hydrophilic B-block may be branched. The hydrophobic A-block may comprise hydrophobic hydrocarbon chains branching therefrom. The hydrophobic hydrocarbon chains may be of shorter chain lengths than the hydrophobic hydrocarbon A-block. The hydrophilic B-block may comprise further hydrophilic B-blocks branching therefrom.

In some embodiments, the additive is a B-A-B tri-block copolymer comprising a hydrophobic hydrocarbon A-block and hydrophilic B-blocks.

In other embodiments, the additive is graft copolymer. The graft copolymer may preferably comprise a hydrophobic hydrocarbon A-block with hydrophilic B-blocks branching therefrom.

In further embodiments, the additive is a brush copolymer. The additive may comprise a single hydrophilic B-block with more than one hydrophobic hydrocarbon A-block branching from an end thereof. The B-block may comprise 2, 3, 4, 5, 6, 7, 8, 9, 10, or more hydrophobic A-blocks branching from the end thereof.

In all of the above embodiments, the or each hydrophilic B-block may comprise a hydrophilic oligomer, i.e. a homo- or co-oligomer comprising at least one monomer unit. The hydrophilic oligomer may comprise between 2 and 10 monomer units. The at least one monomer unit may be selected from the group comprising: alkylene oxides, alkylene glycols, epihalohydrins, unsaturated carboxylic acids, alkylene imines, lactones, vinyl alcohol, and vinyl alkanoates. The at least one monomer unit may be preferably selected from the group comprising: ethylene oxide, propylene oxide, ethylene glycol, propylene glycol, epichlorohydrin, acrylic acid, methacrylic acid, ethylene imine, caprolactone, vinyl alcohol, and vinyl acetate. In some embodiments, the at least one monomer unit comprises alkylene oxide groups independently selected from ethylene oxide and propylene oxide, and in preferred embodiments, all of the monomer units are ethylene oxide or all of the monomer units are propylene oxide.

In some embodiments, the A-block comprises a hydrocarbon chain block of the formula $CH_3CH_2(CH_2CH_2)_a$ where "a" represents a number of repeat units.

In some embodiments, "a" is at least 19, or at least 20, 21, 22, 23, 24, 25, or at least 26.

In further embodiments, the additive is a star-block or a multi-block copolymer comprising hydrophilic and hydrophobic monomer units.

In some embodiments, the lubricious additive amphiphilic molecule has a hydrophilic-lipophilic balance (HLB) below 8, 7, 6, 5, 4, 3, 2 or below 1, preferably between 0.5 and 8, 0.5 and 7, 0.5 and 6, 0.5 and 5, 0.5 and 4, or between 0.5 and 3, especially between 0.5 and 2. Statements of invention relating to the HLB of the amphiphilic molecule of the first aspect of the invention may also be applied to the amphiphilic molecule of the second aspect of the invention.

Statements of invention relating to the intermittent catheter of the first, third and fourth aspects of the invention or to any of its components may also be applied to the second aspect of the invention.

According to a third aspect of the invention, there is provided an intermittent catheter comprising a hollow polymeric tubular body comprising a base polymer and a lubricious additive, wherein the lubricious additive is an amphiphilic molecule comprising at least one hydrophobic and at least one hydrophilic portion, and wherein the molecular weight ratio of the at least one hydrophobic portion to the at least one hydrophilic portion is at least 6.

A lubricious additive with such a molecular weight ratio of the hydrophobic to hydrophilic portions provides a ratio of the degree to which it is hydrophobic and hydrophilic which allows for hydrophobic-hydrophobic interactions between the hydrophobic portion and the base polymer to overcome the hydrophilic-hydrophilic interactions between the hydrophilic portion and a hydrophilic external environment (often comprising a transportation or wetting agent aqueous solution). This allows for reduced migration of the additive out of the catheter. Such ratios nonetheless also allow the hydrophilic portion of the additive to seek towards an outer surface of the intermittent catheter due to its affinity with the hydrophilic external environment and its incompatibility with the hydrophobic base polymer. When the hydrophilic portion of the amphiphilic additive is present at or on the outer surface of the intermittent catheter, it enables wetting of the outer surface simply by applying water or wiping with a wet wipe to create a lubricious coating, which makes the catheter easier and less painful to use, especially for individuals practicing self-catheterisation.

In some embodiments, the molecular weight ratio of the at least one hydrophobic portion to the at least one hydrophilic portion of the additive is at least 6.2, or at least 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 11.2, 11.4, 11.6, 11.8, 12, 12.2, 12.4, 12.6, 12.8, 13, 13.2, 13.4, 13.6, 13.8, 14, 14.2, 14.4, 14.6, 14.8, or at least 15.

In some embodiments, the molecular weight ratio of the at least one hydrophobic portion to the at least one hydrophilic portion of the additive is at least 7, at least 8, or at least 8.5.

In some embodiments, the molecular weight ratio of the at least one hydrophobic portion to the at least one hydrophilic portion of the additive is no greater than 50, or no greater than 45, 40, 35, 30, 25, or no greater than 20.

In some embodiments, the molecular weight ratio of the at least one hydrophobic portion to the at least one hydrophilic portion of the additive is between 6-15.

The molecular weight ratio of the at least one hydrophobic portion to the at least one hydrophilic portion of the additive may be between 6.5-15, or between 7-15, 7.5-15, 8-15, 8.5-15, 9-15, 9.5-15, 10-15, 10.5-15, 11-15, 11.5-15, 12-15, 12.5-15, 13-15, 13.5-15, 14-15, or between 14.5-15.

The molecular weight ratio of the at least one hydrophobic portion to the at least one hydrophilic portion of the additive may be between 6-14.5, or between 6-14, 6-13.5, 6-13, 6-12.5, 6-12, 6-11.5, 6-11, 6-10.5, 6-10, 6-9.5, 6-9, 6-8.5, 6-8, 6-7.5, 6-7, or between 6-6.5.

The molecular weight ratio of the at least one hydrophobic portion to the at least one hydrophilic portion of the additive may be between 6.5-14.5, or between 7-14.5, 7.5-14.5, 8-14.5, 8.5-14.5, 9-14.5, 9.5-14.5, 10-14.5, 10.5-14.5, 11-14.5, 11.5-14.5, 12-14.5, 12.5-14.5, 13-14.5, 13.5-14.5, 14-14.5, 6.5-14, 7-14, 7.5-14, 8-14, 8.5-14, 9-14, 9.5-14, 10-14, 10.5-14, 11-14, 11.5-14, 12-14, 12.5-14, 13-14, 13.5-14, 6.5-13.5, 7-13.5, 7.5-13.5, 8-13.5, 8.5-13.5, 9-13.5, 9.5-13.5, 10-13.5, 10.5-13.5, 11-13.5, 11.5-13.5, 12-13.5, 12.5-13.5, 13-13.5, 6.5-13, 7-13, 7.5-13, 8-13, 8.5-13, 9-13, 9.5-13, 10-13, 10.5-13, 11-13, 11.5-13, 12-13, 12.5-13, 6.5-12.5, 7-12.5, 7.5-12.5, 8-12.5, 8.5-12.5, 9-12.5, 9.5-12.5, 10-12.5, 10.5-12.5, 11-12.5, 11.5-12.5, 12-12.5, 6.5-12, 7-12, 7.5-12, 8-12, 8.5-12, 9-12, 9.5-12, 10-12, 10.5-12, 11-12, 11.5-12, 6.5-11.5, 7-11.5, 7.5-11.5, 8-11.5, 8.5-11.5, 9-11.5, 9.5-11.5, 10-11.5, 10.5-11.5, 11-11.5, 6.5-11, 7-11, 7.5-11, 8-11, 8.5-11, 9-11, 9.5-11, 10-11, 10.5-11, 6.5-10.5, 7-10.5, 7.5-10.5, 8-10.5, 8.5-10.5, 9-10.5, 9.5-10.5, 10-10.5, 6.5-10, 7-10, 7.5-10, 8-10, 8.5-10, 9-10, 9.5-10, 6.5-9.5, 7-9.5, 7.5-9.5, 8-9.5, 8.5-9.5, 9-9.5, 6.5-9, 7-9, 7.5-9, 8-9, 8.5-9, 6.5-8.5, 7-8.5, 7.5-8.5, 8-8.5, 6.5-8, 7-8, 7.5-8, 6.5-7.5, 7-7.5, or between 6.5-7.

The lubricious additive may comprise an amphiphilic molecule that is polymeric or oligomeric.

In some embodiments, the additive is an A-B block copolymer comprising a hydrophobic hydrocarbon A-block and a hydrophilic B-block. In some embodiments, one or both of the hydrophobic hydrocarbon A-block and the hydrophilic B-block may be branched. The hydrophobic A-block may comprise hydrophobic hydrocarbon chains branching therefrom. The hydrophobic hydrocarbon chains may be of shorter chain lengths than the hydrophobic hydrocarbon A-block. The hydrophilic B-block may comprise further hydrophilic B-blocks branching therefrom.

In some embodiments, the additive is a B-A-B tri-block copolymer comprising a hydrophobic hydrocarbon A-block and hydrophilic B-blocks.

In further embodiments, the additive is a graft copolymer. The graft copolymer may preferably comprise a hydrophobic hydrocarbon A-block with hydrophilic B-blocks branching therefrom.

In further embodiments, the additive is a brush copolymer. The additive may comprise a single hydrophilic B-block with more than one hydrophobic hydrocarbon A-block branching from an end thereof. The B-block may comprise 2, 3, 4, 5, 6, 7, 8, 9, 10, or more hydrophobic A-blocks branching from the end thereof.

In all of the above embodiments, the or each hydrophilic B-block may comprise a hydrophilic oligomer, i.e. a homo- or co-oligomer comprising at least one monomer unit. The hydrophilic oligomer may comprise between 2 and 10 monomer units. The at least one monomer unit may be selected from the group comprising: alkylene oxides, alkylene glycols, epihalohydrins, unsaturated carboxylic acids, alkylene imines, lactones, vinyl alcohol, and vinyl alkanoates. The at least one monomer unit may be preferably selected from the group comprising: ethylene oxide, propylene oxide, ethylene glycol, propylene glycol, epichlorohydrin, acrylic acid, methacrylic acid, ethylene imine, caprolactone, vinyl alcohol, and vinyl acetate. In some embodiments, the at least one monomer unit comprises alkylene oxide groups independently selected from ethylene oxide and propylene oxide, and in preferred embodiments, all of the monomer units are ethylene oxide or all of the monomer units are propylene oxide.

In some embodiments, the A-block comprises a hydrocarbon chain block of the formula $CH_3CH_2(CH_2CH_2)_a$ where "a" represents a number of repeat units.

In some embodiments, "a" is at least 18, or at least 19, 20, 21, 22, 23, 24, 25, or at least 26.

In further embodiments, the additive is a star-block or a multi-block copolymer comprising hydrophilic and hydrophobic monomer units.

In some embodiments, the lubricious additive amphiphilic molecule has a hydrophilic-lipophilic balance (HLB) below 8, 7, 6, 5, 4, 3, 2 or below 1, preferably between 0.5 and 8, 0.5 and 7, 0.5 and 6, 0.5 and 5, 0.5 and 4, or between 0.5 and 3, especially between 0.5 and 2. Statements of invention relating to the HLB of the amphiphilic molecule of the first aspect of the invention may also be applied to the amphiphilic molecule of the third aspect of the invention.

Statements of invention relating to the intermittent catheter of the first, second and fourth aspects of the invention or to any of its components may also be applied to the third aspect of the invention.

According to a fourth aspect of the invention, there is provided an intermittent catheter comprising a hollow polymeric tubular body comprising a base polymer and a lubricious additive, wherein the lubricious additive is an amphiphilic molecule having a hydrophobic portion comprising an alkyl group of at least 53 carbon atoms.

The amphiphilic lubricious additive comprises a hydrophobic portion and a hydrophilic portion. A lubricious additive with a hydrophobic portion comprising an alkyl group of at least 53 carbon atoms provides for sufficient hydrophobicity to allow for hydrophobic-hydrophobic interactions between the hydrophobic portion and the base polymer to overcome the hydrophilic-hydrophilic interactions between the hydrophilic portion and a hydrophilic external environment (often comprising a transportation or wetting agent aqueous solution). This allows for reduced migration of the additive out of the catheter, even when the catheter is stored in water. Such a hydrophobic portion nonetheless also allows the hydrophilic portion of the additive to seek towards an outer surface of the intermittent catheter due to its affinity with the hydrophilic external environment and its incompatibility with the hydrophobic base polymer. When the hydrophilic portion of the amphiphilic additive is present at or on the outer surface of the intermittent catheter, it enables wetting of the outer surface simply by applying water or wiping with a wet wipe to create a lubricious coating, which makes the catheter easier and less painful to use, especially for individuals practicing self-catheterisation.

The lubricious additive may comprise an amphiphilic molecule that is polymeric or oligomeric.

In some embodiments, the hydrophobic portion comprises an alkyl group comprising a carbon chain of at least 53 carbon atoms.

In some embodiments, the hydrophobic portion comprises an alkyl group of at least 54 carbon atoms, or of at least 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or of at least 150 carbon atoms. In some embodiments, the carbon atoms may comprise a carbon chain.

In some embodiments, the hydrophobic portion comprises an alkyl group of no more than 200 carbon atoms, or of no more than 200, 199, 198, 197, 196, 195, 194, 193, 192, 191, 190, 189, 188, 187, 186, 185, 184, 183, 182, 181, 180, 179, 178, 177, 176, 175, 174, 173, 172, 171, 170, 169, 168, 167, 166, 165, 164, 163, 162, 161, 160, 159, 158, 157, 156, 155, 154, 153, 152, or of no more than 151 carbon atoms. In some embodiments, the carbon atoms may comprise a carbon chain.

In some embodiments, the hydrophobic portion comprises an alkyl group of between 53-200 carbon atoms.

In some embodiments, the hydrophobic portion comprises an alkyl group of between 55-200 carbon atoms, or of between 60-200, 70-200, 80-200, 90-200, 100-200, 110-200, 120-200, 130-200, 140-200, 150-200, 160-200, 170-200, 180-200, or of between 190-200 carbon atoms. In some embodiments, the carbon atoms may comprise a carbon chain.

In some embodiments, the hydrophobic portion comprises an alkyl group of between 53-190 carbon atoms, or of between 53-180, 53-170, 53-160, 53-150, 53-140, 53-130, 53-120, 53-110, 53-100, 53-90, 53-80, 53-70, 53-60, or of between 53-55 carbon atoms. In some embodiments, the carbon atoms may comprise a carbon chain.

In further embodiments, the hydrophobic portion comprises an alkyl group of between 55-190 carbon atoms, or of between 60-190, 70-190, 80-190, 90-190, 100-190, 110-190, 120-190, 130-190, 140-190, 150-190, 160-190, 170-190, 180-190, 55-180, 60-180, 70-180, 80-180, 90-180, 100-180, 110-180, 120-180, 130-180, 140-180, 150-180, 160-180, 170-180, 55-170, 60-170, 70-170, 80-170, 90-170, 100-170, 110-170, 120-170, 130-170, 140-170, 150-170, 160-170, 55-160, 60-160, 70-160, 80-160, 90-160, 100-160, 110-160, 120-160, 130-160, 140-160, 150-160, 55-150, 60-150, 70-150, 80-150, 90-150, 100-150, 110-150, 120-150, 130-150, 140-150, 55-140, 60-140, 70-140, 80-140, 90-140, 100-140, 110-140, 120-140, 130-140, 55-130, 60-130, 70-130, 80-130, 90-130, 100-130, 110-130, 120-130, 55-120, 60-120, 70-120, 80-120, 90-120, 100-120, 110-120, 55-110, 60-110, 70-110, 80-110, 90-110, 100-110, 55-100, 60-100, 70-100, 80-100, 90-100, 55-90, 60-90, 70-90, 80-90, 55-80, 60-80, 70-80, 55-70, 60-70, or of between 55-60 carbon atoms. In some embodiments, the carbon atoms may comprise a carbon chain.

In some embodiments, the additive comprises an A-B block copolymer comprising a hydrophobic hydrocarbon A-block and a hydrophilic B-block. In some embodiments, one or both of the hydrophobic hydrocarbon A-block and the hydrophilic B-block may be branched. The hydrophobic A-block may comprise hydrophobic hydrocarbon chains branching therefrom. The hydrophobic hydrocarbon chains may be of shorter chain lengths than the hydrophobic hydrocarbon A-block. The hydrophilic B-block may comprise further hydrophilic B-blocks branching therefrom.

In some embodiments, the additive is a B-A-B tri-block copolymer comprising a hydrophobic hydrocarbon A-block and hydrophilic B-blocks.

In further embodiments, the additive is a graft copolymer. The graft copolymer may preferably comprise a hydrophobic hydrocarbon A-block with hydrophilic B-blocks branching therefrom.

In further embodiments, the additive is a brush copolymer. The additive may comprise a single hydrophilic B-block with more than one hydrophobic hydrocarbon A-block branching from an end thereof. The B-block may comprise 2, 3, 4, 5, 6, 7, 8, 9, 10, or more hydrophobic A-blocks branching from the end thereof.

In all of the above embodiments, the or each hydrophilic B-block may comprise a hydrophilic oligomer, i.e. a homo- or co-oligomer comprising at least one monomer unit. The hydrophilic oligomer may comprise between 2 and 10 monomer units. The at least one monomer unit may be selected from the group comprising: alkylene oxides, alkylene glycols, epihalohydrins, unsaturated carboxylic acids, alkylene imines, lactones, vinyl alcohol, and vinyl alkanoates. The at least one monomer unit may be preferably selected from the group comprising: ethylene oxide, propylene oxide, ethylene glycol, propylene glycol, epichlorohydrin, acrylic acid, methacrylic acid, ethylene imine, caprolactone, vinyl alcohol, and vinyl acetate. In some embodiments, the at least one monomer unit comprises alkylene oxide groups independently selected from ethylene oxide and propylene oxide, and in preferred embodiments, all of the monomer units are ethylene oxide or all of the monomer units are propylene oxide.

In some embodiments, the A-block comprises a hydrocarbon chain block of the formula $CH_3CH_2(CH_2CH_2)_a$ where "a" is at least 26.

In some embodiments, "a" is at least 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or at least 80.

In some embodiments, "a" is no more than 100, 99, 98, 97, 96, 95, 94, 93, 92, 91, 90, 89, 88, 87, 86, 85, 84, 83, 82, or no more than 81.

In some embodiments, "a" is between 26-100.

In some embodiments, "a" is between 30-100, or between 40-100, 50-100, 60-100, 70-100, 80-100, or between 90-100.

In some embodiments, "a" is between 26-90, or between 26-80, 26-70, 26-60, 26-50, 26-40, or between 26-30.

In further embodiments, "a" is between 30-90, or between 40-90, 50-90, 60-90, 70-90, 80-90, 30-80, 40-80, 50-80, 60-80, 70-80, 30-70, 40-70, 50-70, 60-70, 30-60, 40-60, 50-60, 30-50, 40-50, or between 30-40.

In further embodiments, the additive is a star-block or a multi-block copolymer comprising hydrophilic and hydrophobic monomer units.

In some embodiments, the B-block is a hydrophilic oligomer comprising between 2 and 10 monomer units, the monomer units optionally derived from monomers selected from the group comprising: alkylene oxides, alkylene glycols, epihalohydrins, unsaturated carboxylic acids, alkylene imines, lactones, vinyl alcohol, and vinyl alkanoates.

The monomer units may be preferably selected from the group comprising: ethylene oxide, propylene oxide, ethylene glycol, propylene glycol, epichlorohydrin, acrylic acid, methacrylic acid, ethylene imine, caprolactone, vinyl alcohol, and vinyl acetate. In some embodiments, the monomer units comprise alkylene oxide groups independently selected from ethylene oxide and propylene oxide, and in preferred embodiments, all of the monomer units are ethylene oxide or all of the monomer units are propylene oxide.

In some embodiments, the lubricious additive amphiphilic molecule has a hydrophilic-lipophilic balance (HLB) below 8, 7, 6, 5, 4, 3, 2 or below 1, preferably between 0.5 and 8, 0.5 and 7, 0.5 and 6, 0.5 and 5, 0.5 and 4, or between 0.5 and 3, especially between 0.5 and 2. Statements of invention relating to the HLB of the amphiphilic molecule of the first aspect of the invention may also be applied to the amphiphilic molecule of the fourth aspect of the invention.

The following statements apply to each of the first, second, third and fourth aspects of the invention.

At least some of the additive may be at or on the outer surface of the body. By "at the outer surface", it is meant that at least a portion of the additive forms part of the surface or protrudes from the surface. In some embodiments, part of the additive is retained or anchored in the body while part of the additive forms part of or protrudes from the outer surface of the body.

The outer surface may comprise at least one of the group comprising: the external facing surface of the body, the lumen of the body, and any eyelets present on the body. In preferred embodiments, the outer surface is the external-facing surface of the body and/or the inner lumen. In some embodiments, the outer surface may comprise the external-facing surface of the body of the catheter, the inner lumen, and the eyelets.

The additive may be concentrated at or on the outer surface of the body. For example, at least 25%, 30%, 35%, 40%, 45%, 50%, 55%, 60%, 65%, 70%, 75%, or at least 80% of the number of molecules of the additive may be at or on the outer surface of the body.

In some embodiments, at least 25%, 30%, 35%, 40%, 45%, 50%, 55%, 60%, 65%, 70%, 75% or at least 80% of the number of molecules of additive may have hydrophilic portions that are at or on the outer surface of the body.

In some embodiments, the additive is located at and/or on at least 50, 55, 60, 65, 70, 75, 80, 85, 90, 95, 96, 97, 98 or at least 99% of the outer surface area of the polymeric tubular body, preferably at least 75% or at least 90% of the outer surface area of the polymeric tubular body or between 75% and 100% of the outer surface area.

In some embodiments, the additive comprises a concentration of at least 0.1, 0.2, 0.3. 0.4. 0.5, 0.75, 1, 2, 3, 4, 5, 10, 15 or at least 20%, preferably between 0.1-20%, and more preferably between 0.5-15% or 0.5-5% by weight of the combination of base polymer and additive.

In some embodiments, the base polymer comprises a polymer selected from the group comprising: polyvinyl chloride, polytetrafluoroethylene, polyolefins, latex, silicones, synthetic rubbers, polyurethanes, polyesters, polyacrylates, polyamides, thermoplastic elastomeric materials, styrene block copolymers, polyether block amide, thermoplastic vulcanizates, thermoplastic copolyesters, thermoplastic polyamides, styrene-butadiene copolymer (SBC), styrene-ethylene-butylene-styrene copolymer (SEBS), and water disintegrable or enzymatically hydrolysable material, or combinations, blends or copolymers of any of the above materials.

In preferred embodiments, the base polymer comprises a polymer selected from the group comprising: polyolefins, polyesters, polyacrylates, polyamides, thermoplastic elastomeric material, polyether block amide, thermoplastic vulcanizates, thermoplastic copolyesters, thermoplastic polyamides, fluororubber, and water disintegrable or enzymatically hydrolysable material or combinations, blends or copolymers of any of the above materials.

In some embodiments, said water disintegrable or enzymatically hydrolysable material comprises a material of the group comprising: polyvinyl alcohol, extrudable polyvinyl alcohol, polyacrylic acids, polylactic acid, polyesters, polyglycolide, polyglycolic acid, poly lactic-co-glycolic acid, polylactide, amines, polyacrylamides, poly(N-(2-Hydroxypropyl) methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, poly-ethers, polyethylene oxide, blends of polyethylene-polypropylene glycol, carboxymethyl cellulose, guar gum, locust bean gum, hydroxypropyl cellulose, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly-caprolactone, poly(p-dioxanone), or combinations, blends or copolymers of any of the above materials.

In other preferred embodiments, the base polymer comprises a polymer selected from the group comprising: polyolefins, polyvinyl chloride, polyurethane, styrene-butadiene copolymer (SBC), styrene-ethylene-butylene-styrene copolymer (SEBS), and thermoplastic elastomeric material or combinations, blends or copolymers of any of the above materials.

In some preferred embodiments, the base polymer comprises a polyolefin, especially polyethylene and/or polypropylene.

In some preferred embodiments, the base polymer comprises a thermoplastic elastomeric material. The base polymer may comprise a thermoplastic polyolefin.

In preferred embodiments, the base polymer is hydrophobic or partly hydrophobic.

The thermoplastic base polymer may comprise a hydrophobic polymer selected from the group comprising: Accurel™, Styroflex™, Styrolux™, MelifleX™, and Mediprene™.

The thermoplastic base polymer may comprise Estane™ 58315, which is both hydrophobic and hydrophilic.

In some embodiments, an outer surface of the polymeric tubular body comprises a separate or further lubricating agent or bacteria-repellent agent at and/or on the surface, in addition to the additive. The separate or further lubricating agent or bacteria-repellent agent may be bonded at and/or on the surface.

In some embodiments, said further lubricating agent or bacteria-repellent agent is formed from a coating material selected from the group comprising: silver-based, polytetrafluoroethylene, hydrogel, silicone, lecithin, salicylic acid, minocycline, rifampin, fluorinated ethylene propylene, polyvinylidone, polyvinyl compounds, polylactames, polyvinyl pyrrolidones, polysaccharides, heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, polyethylene oxides, polyvinyl alcohols, polyamides, polyacrylic acid, hydroxy ethylmethyl acrylate, polymethylvinyl ether, maleinic acid anyhydride, penicillin, neomycin sulfate, cephalothin, Bacitracin, phenoxymethyl penicillin, lincoymycin hydrochloride, sulfadiazine, methyl sulfadiazine, succinoylsulfathiazole, phthalylsulfathiazde, sulfacetamine, procaine penicillin, streptomycin, aureomycin, terramycin, terramycin, quaternary ammonium halides, cetyl pyridinium chloride, triethyl dodecyl ammonium bromide, hexachlorophene and nitrofurazone, or any combination thereof.

According to a fifth aspect of the invention, there is provided a method of reducing migration of an additive from a surface of an intermittent catheter, the intermittent catheter comprising a hollow polymeric tubular body comprising a base polymer and a lubricious additive comprising an amphiphilic molecule having a hydrophilic-lipophilic balance below 8, wherein the method comprises mixing the lubricious additive with the base polymer before or during formation of the hollow polymeric tubular body.

The additive may comprise any additive of the first aspect of the invention.

The intermittent catheter may comprise any intermittent catheter of the first aspect of the invention. Statements of invention relating to the intermittent catheter of the first aspect of the invention or to any of its components may also be applied to the fifth aspect of the invention.

According to a sixth aspect of the invention, there is provided a method of reducing migration of an additive from a surface of an intermittent catheter, the intermittent catheter comprising a hollow polymeric tubular body comprising a base polymer and a lubricious additive, wherein the lubricious additive is an amphiphilic molecule comprising hydrophobic and hydrophilic monomer units, and wherein the additive has a hydrophobic to hydrophilic monomer unit ratio of at least 10.

The additive may comprise any additive of the second aspect of the invention.

The intermittent catheter may comprise any intermittent catheter of the second aspect of the invention. Statements of invention relating to the intermittent catheter of the second aspect of the invention or to any of its components may also be applied to the sixth aspect of the invention.

According to a seventh aspect of the invention, there is provided a method of reducing migration of an additive from a surface of an intermittent catheter, the intermittent catheter comprising a hollow polymeric tubular body comprising a base polymer and a lubricious additive, wherein the lubricious additive is an amphiphilic molecule comprising at least one hydrophobic and at least one hydrophilic portion, and wherein the molecular weight ratio of the at least one hydrophobic portion to the at least one hydrophilic portion is at least 6.

The additive may comprise any additive of the third aspect of the invention.

The intermittent catheter may comprise any intermittent catheter of the third aspect of the invention. Statements of invention relating to the intermittent catheter of the third aspect of the invention or to any of its components may also be applied to the seventh aspect of the invention According to an eighth aspect of the invention, there is provided a method of reducing migration of an additive from a surface of an intermittent catheter, the intermittent catheter comprising a hollow polymeric tubular body comprising a base polymer and a lubricious additive comprising an amphiphilic molecule having a hydrophobic portion comprising an alkyl group of at least 53 carbon atoms, wherein the method comprises mixing the lubricious additive with the base polymer before or during formation of the hollow polymeric tubular body.

The additive may comprise any additive of the fourth aspect of the invention.

The intermittent catheter may comprise any intermittent catheter of the fourth aspect of the invention. Statements of invention relating to the intermittent catheter of the fourth aspect of the invention or to any of its components may also be applied to the eighth aspect of the invention.

The following statements apply to the fifth, sixth, seventh, and eighth aspects of the invention.

Formation of the hollow polymeric tubular body may comprise a melt-extrusion or injection-moulding procedure.

The base polymer and/or additive, preferably both, may be provided in granulate or powder form. The method may comprise mixing the granulate or powder base polymer and additive to form a mixture, and melt-extruding or injection-moulding the mixture to form the hollow polymeric tubular intermittent catheter body.

In some embodiments, the method comprises melting the mixture of the base polymer and additive to form a second mixture before melt-extruding or injection-moulding the second mixture to form the hollow polymeric tubular intermittent catheter body.

According to a ninth aspect of the invention there is provided a packaged intermittent catheter of the first aspect of the invention comprising a packaging container in which is located an intermittent catheter of the first aspect of the invention, and optionally a wetting agent.

According to a tenth aspect of the invention there is provided a packaged intermittent catheter of the second aspect of the invention comprising a packaging container in which is located an intermittent catheter of the second aspect of the invention, and optionally a wetting agent.

According to an eleventh aspect of the invention there is provided a packaged intermittent catheter of the third aspect of the invention comprising a packaging container in which is located an intermittent catheter of the third aspect of the invention, and optionally a wetting agent.

According to a twelfth aspect of the invention there is provided a packaged intermittent catheter of the fourth aspect of the invention comprising a packaging container in which is located an intermittent catheter of the fourth aspect of the invention, and optionally a wetting agent.

The wetting agent of any of the ninth to twelfth aspects of the invention, when present, may surround the intermittent catheter or may be separated from the intermittent catheter within the packaging, for example by providing the wetting agent in a separate container within the packaging container.

The wetting agent of any of the ninth to twelfth aspects of the invention may comprise an aqueous solution or water. The aqueous solution may comprise one or more ingredients selected from the group comprising a salt, a buffer, an antibiotic, an active agent (which may be a medicament) and a thickening agent.

DETAILED DESCRIPTION OF THE INVENTION

In order that the invention may be more clearly understood embodiments thereof will now be described, by way of example only:

Example 1

A first embodiment of an intermittent catheter of the invention comprises an intermittent catheter comprising a hollow polymeric tubular body comprising a base polymer formed of thermoplastic polypropylene and further comprising an amphiphilic additive of the formula $CH_3CH_2(CH_2CH_2)_{27}(OCH_2CH_2)_6OH$.

The amphiphilic additive comprises an HLB value of approximately 5.

The additive comprises a polyethylene oxide hydrophilic portion which seeks towards the outer surface of the body due to its incompatibility with the base polymer, the outer surface becoming lubricious as a result. The additive also comprises a polyethylene lipophilic and hydrophobic portion which ensures that the hydrophilic portion is secured to the base polymer.

The intermittent catheter may be prepared as described in U.S. Pat. Nos. 10,058,638 B2 and 9,186,438 B2.

The intermittent catheter is used in the conventional manner.

The HLB value of 5 provides a beneficial ratio of the degree to which the additive is hydrophobic and hydrophilic that allows for hydrophobic-hydrophobic interactions between the hydrophobic portion and the base polymer to overcome the hydrophilic-hydrophilic interactions between the hydrophilic portion and a hydrophilic external environment (often comprising a transportation or wetting agent aqueous solution). This allows for reduced migration of the additive out of the catheter, even when the surface of the catheter is scraped. Such an HLB value nonetheless also allows the hydrophilic portion of the additive to seek towards the outer surface of the intermittent catheter due to its affinity with the hydrophilic external environment and its incompatibility with the hydrophobic base polymer. The amphiphilic additive at the outer surface of the intermittent catheter body confers high lubricity to the outer surface of the intermittent catheter, making it both easier to insert and remove.

The intermittent catheter of Example 1 conferred reduced migration of the amphiphilic additive from the surface of the catheter during both storage/transport and through use of the catheter compared with a similar additive with an HLB greater than 8. It also provided reduced resistance to abrasion of the additive from the surface of the catheter on contact with external bodies.

Example 2

A second embodiment of an intermittent catheter of the invention comprises an intermittent catheter comprising a hollow polymeric tubular body comprising a base polymer formed of thermoplastic polyethylene and further comprising an amphiphilic additive of the formula $CH_3CH_2(CH_2CH_2)_{30}(OCH_2CH_2)_2OH$.

The amphiphilic additive comprises an HLB value of approximately 2.

The amphiphilic additive has a hydrophobic to hydrophilic monomer unit ratio of 15.5.

The molecular weight ratio of the hydrophobic to the hydrophilic portion of the additive is approximately 8.3.

The additive comprises a polyethylene oxide hydrophilic portion which seeks towards the outer surface of the body due to its incompatibility with the base polymer, the outer surface becoming lubricious as a result. The additive also comprises a polyethylene lipophilic and hydrophobic portion which ensures that the hydrophilic portion is secured to the base polymer.

The intermittent catheter may be prepared as described in U.S. Pat. Nos. 10,058,638 B2 and 9,186,438 B2.

The intermittent catheter is used in the conventional manner.

The mechanism of action of the amphiphilic additive is as described in Example 1 above.

The intermittent catheter of Example 2 conferred reduced migration of the amphiphilic additive from the surface of the catheter during both storage/transport and through use of the catheter, compared with a similar additive with less than 53 carbons in the hydrophobic portion of the amphiphilic molecule. It also provided reduced resistance to abrasion of the additive from the surface of the catheter on contact with external bodies.

Example 3

A third embodiment of an intermittent catheter of the invention comprises an intermittent catheter comprising a hollow polymeric tubular body comprising a base polymer formed of thermoplastic polyethylene and further comprising an amphiphilic additive of the formula $CH_3CH_2(CH_2CH_2)_{21}(OCH_2CH_2)_2OH$.

The amphiphilic additive has an HLB value of approximately 3.

The amphiphilic additive has a hydrophobic to hydrophilic monomer unit ratio of 11.

The additive comprises a polyethylene oxide hydrophilic portion which seeks towards the outer surface of the body due to its incompatibility with the base polymer, the outer surface becoming lubricious as a result. The additive also comprises a polyethylene lipophilic and hydrophobic portion which ensures that the hydrophilic portion is secured to the base polymer.

The intermittent catheter may be prepared as described in U.S. Pat. Nos. 10,058,638 B2 and 9,186,438 B2.

The intermittent catheter is used in the conventional manner.

The mechanism of action of the amphiphilic additive is as described in Example 1 above.

The intermittent catheter of Example 3 conferred reduced migration of the amphiphilic additive from the surface of the catheter during both storage/transport and through use of the catheter compared with a similar additive with an HLB greater than 8. It also provided reduced resistance to abrasion of the additive from the surface of the catheter on contact with external bodies.

The above embodiments are described by way of example only. Many variations are possible without departing from the scope of the invention as defined in the appended claims.

The invention claimed is:
1. A packaged intermittent catheter unit, comprising:
a packaging container;

a hydrophilic wetting agent disposed in the packaging container;

an intermittent catheter disposed in the packaging container and in contact with the wetting agent, the intermittent catheter comprising a hollow polymeric tubular body comprising a base polymer and a lubricious additive, wherein the base polymer is hydrophobic, wherein the lubricious additive comprises an amphiphilic molecule having a hydrophilic-lipophilic balance below 8 and the amphiphilic molecule comprises hydrophobic and hydrophilic monomer units, and wherein the additive has a hydrophobic to hydrophilic monomer unit ratio of at least 10 to thereby reduce migration of the lubricious additive out of the intermittent catheter; wherein the hydrophobic to hydrophilic monomer unit ratio of at least 10 causes hydrophobic-hydrophobic interactions between the hydrophobic base polymer and hydrophobic portions of the lubricious additive to overcome hydrophilic-hydrophilic interactions between the hydrophilic wetting agent and the hydrophilic portions of the lubricious additive, thereby reducing migration of the lubricious additive out of the catheter and into the hydrophilic wetting agent.

2. The packaged intermittent catheter unit of claim 1, wherein the amphiphilic molecule has a hydrophilic-lipophilic balance below 5.

3. The packaged intermittent catheter unit of claim 1, wherein the amphiphilic molecule comprises at least one hydrophobic and at least one hydrophilic portion, and wherein the molecular weight ratio of the at least one hydrophobic portion to the at least one hydrophilic portion is at least 6.

4. The packaged intermittent catheter unit of claim 1, wherein the additive is an A-B block copolymer comprising a hydrophobic hydrocarbon A-block and a hydrophilic B-block.

5. The packaged intermittent catheter unit of claim 4, wherein the B-block is a hydrophilic oligomer comprising at least one monomer unit, the at least one monomer unit derived from monomers selected from the group comprising: alkylene oxides, alkylene glycols, epihalohydrins, unsaturated carboxylic acids, alkylene imines, lactones, vinyl alcohol, and vinyl alkanoates.

6. The packaged intermittent catheter unit of claim 4, wherein the additive is an A-B block copolymer comprising an A-block comprising a hydrocarbon chain block of the formula $CH_3CH_2(CH_2CH_2)_a$ where "a" is at least 26, and a hydrophilic B-block.

7. The packaged intermittent catheter unit of claim 1, wherein the additive is at and/or on at least 50% of the outer surface area of the polymeric tubular body.

8. A method, comprising:

forming an intermittent catheter comprising a hollow polymeric tubular body comprising a hydrophobic base polymer and a lubricious additive comprising an amphiphilic molecule having a hydrophilic-lipophilic balance below 8, wherein the forming comprises mixing the lubricious additive with the hydrophobic base polymer before or during formation of the hollow polymeric tubular body; and placing the intermittent catheter in a packaging along with a hydrophilic wetting agent;

wherein the additive has a hydrophobic to hydrophilic monomer unit ratio of at least 10 to thereby reduce migration of the lubricious additive out of the intermittent catheter; wherein the hydrophobic to hydrophilic monomer unit ratio of at least 10 causes hydrophobic-hydrophobic interactions between the hydrophobic base polymer and hydrophobic portions of the lubricious additive to overcome hydrophilic-hydrophilic interactions between the hydrophilic wetting agent and the hydrophilic portions of the lubricious additive, thereby reducing migration of the lubricious additive out of the catheter and into the hydrophilic wetting agent.

9. The method of claim 8, wherein the amphiphilic molecule has a hydrophilic-lipophilic balance below 5.

10. The method of claim 8, wherein the additive is an A-B block copolymer comprising a hydrophobic hydrocarbon A-block and a hydrophilic B-block.

11. The method of claim 10, wherein the B-block is a hydrophilic oligomer comprising at least one monomer unit, the at least one monomer unit derived from monomers selected from the group comprising: alkylene oxides, alkylene glycols, epihalohydrins, unsaturated carboxylic acids, alkylene imines, lactones, vinyl alcohol, and vinyl alkanoates.

12. The method of claim 10, wherein the additive is an A-B block copolymer comprising an A-block comprising a hydrocarbon chain block of the formula $CH_3$ $CH_2$ $(CH_2CH_2)_a$ where "a" is at least 26, and a hydrophilic B-block.

13. The method of claim 8, wherein the base polymer and additive are provided in granulate or powder form and the method comprises mixing the granulate or powder base polymer and additive to form a mixture, and melt-extruding or injection-moulding the mixture to form the hollow polymeric tubular body.

14. The method of claim 13, wherein the method comprises melting the mixture of the base polymer and additive to form a second mixture before melt-extruding or injection-moulding the second mixture to form the hollow polymeric tubular body.

15. The method of claim 8, wherein the base polymer comprises a polymer selected from the group comprising:

polyolefins, polyesters, polyacrylates, polyamides, thermoplastic elastomeric material, polyether block amide, thermoplastic vulcanizates, thermoplastic copolyesters, thermoplastic polyamides and fluororubber, or combinations, blends or copolymers of any of the above materials.

16. The method of claim 15, wherein the base polymer comprises a polymer selected from the group comprising: polyolefins, polyvinyl chloride, styrene-butadiene copolymer (SBC), styrene-ethylene-butylene-styrene copolymer (SEBS), and thermoplastic elastomeric material or combinations, blends or copolymers of any of the above materials.

17. The method of claim 8, wherein the additive is at and/or on at least 50% of the outer surface area of the polymeric tubular body.

* * * * *